United States Patent [19]

Woodburn

[11] Patent Number: 4,861,341
[45] Date of Patent: Aug. 29, 1989

[54] SUBCUTANEOUS VENOUS ACCESS DEVICE AND NEEDLE SYSTEM

[76] Inventor: Robert T. Woodburn, 19271 Ravine Dr., New Buffalo, Mich. 49117

[21] Appl. No.: 220,609

[22] Filed: Jul. 18, 1988

[51] Int. Cl.$^4$ .............................................. A61M 5/00
[52] U.S. Cl. .................................... 604/175; 604/272
[58] Field of Search .................. 604/93, 96, 104, 239, 604/272–274, 244, 239, 174, 175, 411, 412

[56] References Cited

U.S. PATENT DOCUMENTS 3,358,684  12/1967  Marshall .............................. 604/272
4,670,008  6/1987  Albertini ............................. 604/272

*Primary Examiner*—Stephen C. Pellegrino
*Attorney, Agent, or Firm*—Richard G. Kinney

[57] ABSTRACT

A system of a subcutaneous venous access device or injection port and needle, wherein the port includes a self-closing septum for repeatedly and periodically receiving a predetermined section of an injection needle, and which septum covers an injection-receiving chamber in communication with a vein. The needle has a non-coring (e.g., "Huber" or removable stylet) point and means for providing a locking configuration such as increased diameter bu smooth outer surface of the needle port-received section, which, when properly inserted, is within the septum or chamber, so as to more securely affix the needle within the port and prevent or decrease the incidence of accidental partial or total removal and the resulting undesirable subcutaneous infiltration of chemicals during infusion. The locking configuration means is, in one embodiment, an expansion section which is maintained (and returned) to a non-expanded configuration by use of a needle core or stylet and which section automatically expands upon removal of the stylet. A second embodiment employs a balloon segment of the needle which is manually inflated in the chamber after setting of the needle in the port. A third and fourth embodiment provide permanent, multi-ridged surfaces which cooperate with the septum to secure the needle in its proper position.

16 Claims, 5 Drawing Sheets

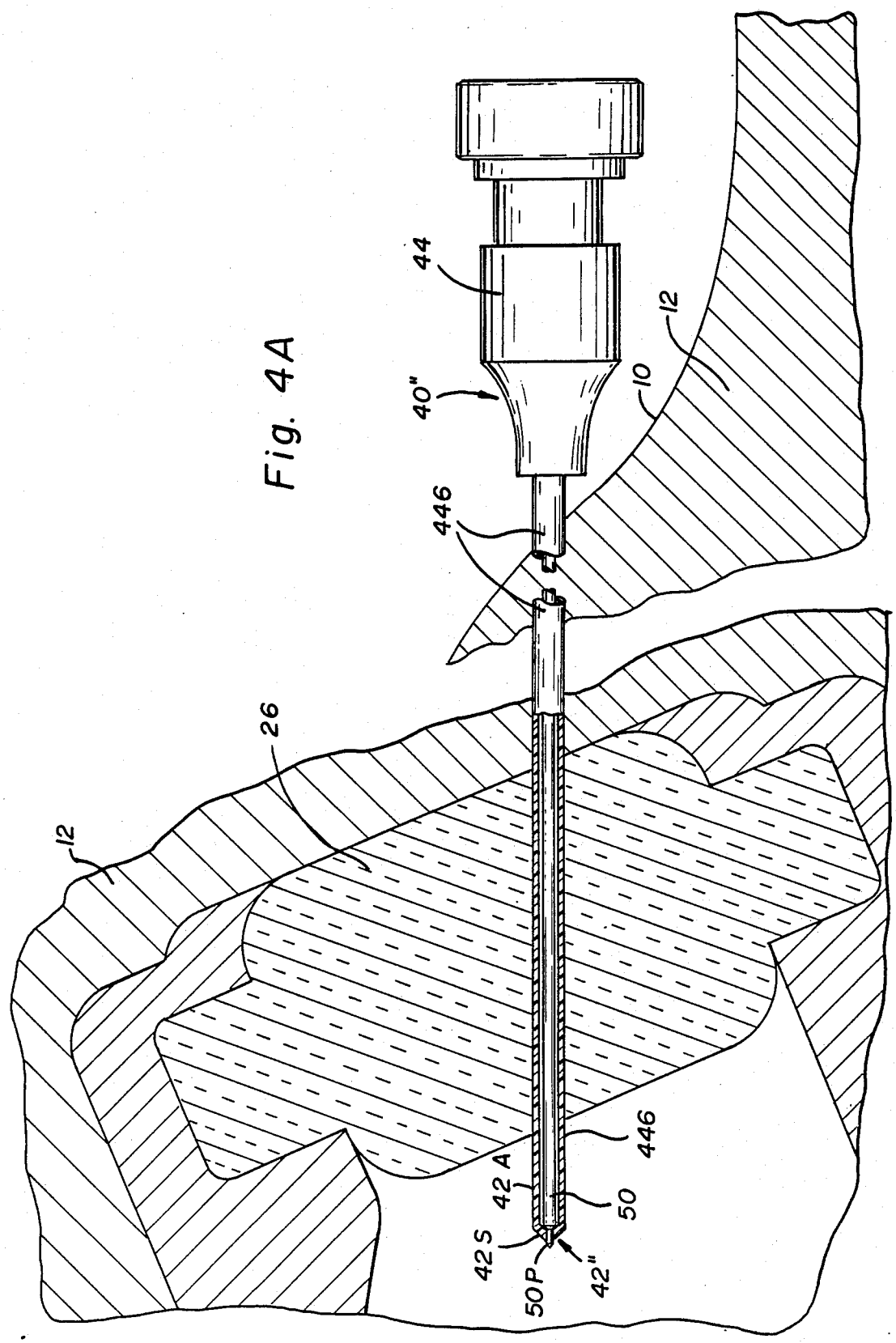

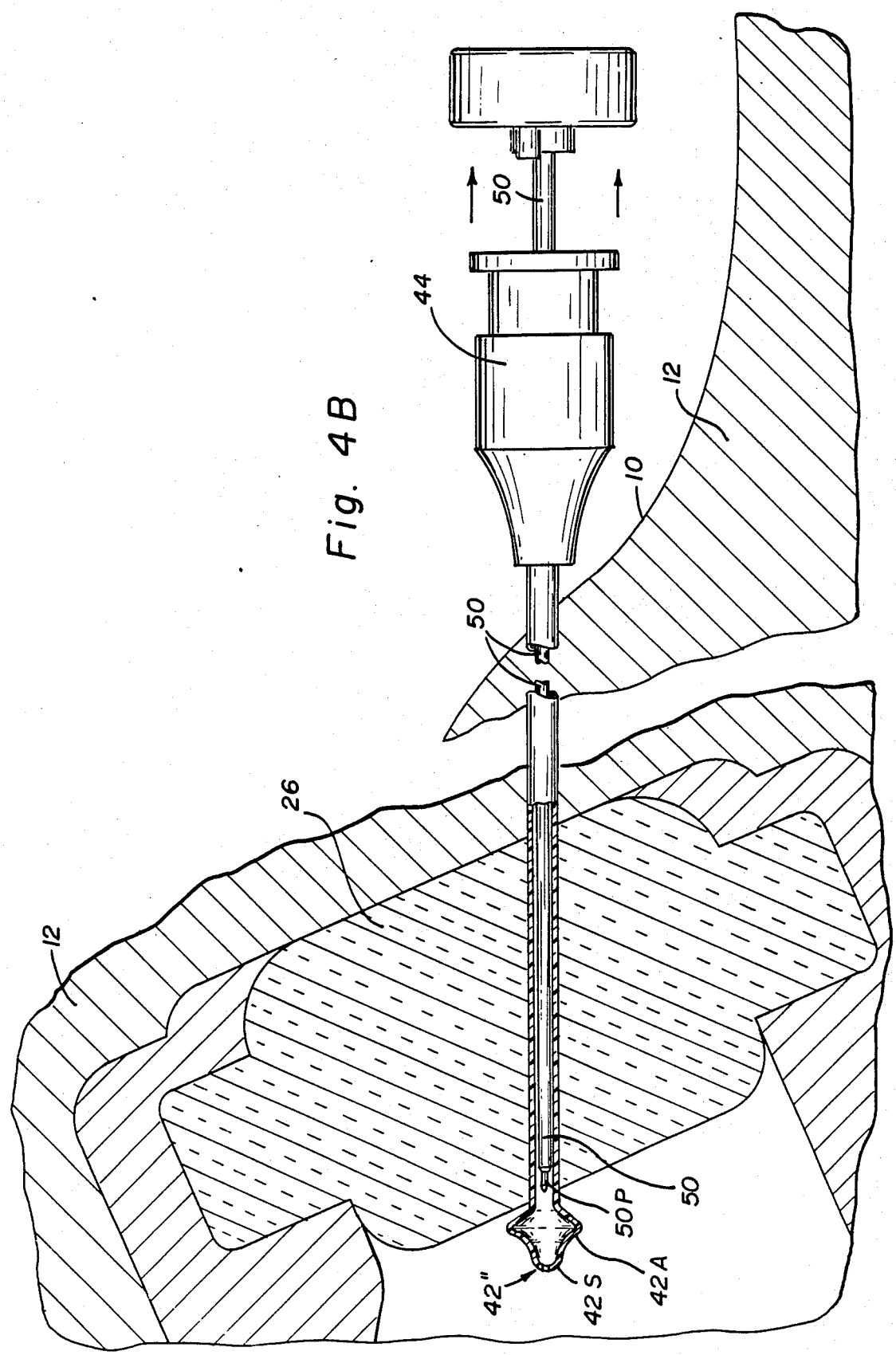

SUBCUTANEOUS VENOUS ACCESS DEVICE AND NEEDLE SYSTEM

FIELD OF THE INVENTION

The present invention is directed to an improved subcutaneous injection port and needle system.

BACKGROUND OF THE INVENTION

Subcutaneous venous access devices or ports are permanently implanted under the skin of a patient to whom it is desired to deliver repeated, periodic intravenous injections or infusions of therapeutic fluids or chemical solutions. Often such devices are used in a program of cancer chemotherapy. The injected chemicals are often toxic and, if injected under the skin rather than into a vein, will result in harm and pain to the patient or decreased absorption of the desired medication. The ports consist of a chamber-defining housing, means for suturing the housing under the skin and a self-sealing septum which allows needles to be passed through the skin and through the septum into the chamber. A catheter tube leads from the chamber and is surgically implanted into a vein. This arrangement allows a needle to be pushed through the patient's skin through the septum and into the chamber and to deliver fluid to and through that chamber into the catheter, directly into the vein. When the needle is properly inserted, the injected or infused chemical solutions are directed into the vein without reaching the skin/or subcutaneous tissue.

Individual administrations of therapeutic fluids in this manner often are accomplished over a relatively long period as infusions lasting hours or days. An infusion pump is often used to supply the fluid under pressure at precise delivery rates. During this time, it sometimes occurs, because of patient movement or otherwise, that prior conventional needles work themselves up and sometimes out of the septum, resulting in the harmful and painful injection of the fluid under the skin of the patient and decreased absorption of the desired medication.

SUMMARY OF THE INVENTION

To overcome or lessen this problem, the present invention provides a subcutaneous venous access device system, which includes a port device defining a chamber, with a septum for allowing a needle input into the chamber and a catheter output for connection into a vein, together with a needle assembly having a needle shaft equipped with means such as one or more bulges or ridges or ballooning sections at the outside surface of its section which is received in the port during use for releasably securing the properly-seated needle against any accidental removal.

The invention, together with the advantages thereof, may best be understood by reference to the following description, taken in connection with the accompanying drawings, in the several figures of which like reference numerals identify like elements.

BRIEF DESCRIPTION OF THE DRAWINGS

FIG. 1A is a sectional view on an enlarged scale of a portion, a needle shaft section and needle point, of the system of FIG. 1 showing various dimensions thereof.

FIGS. 1B and 1C are respectively sectional views of the needle shaft of FIG. 1A as seen from the lines 1B—1B and 1C—1C in that figure.

FIGS. 4A and 4B are each perspective views, partly in section and partly broken away, of a fourth embodiment of the present invention, these figures illustrating moved positions of the same parts.

DETAILED DESCRIPTION

Figure 1:
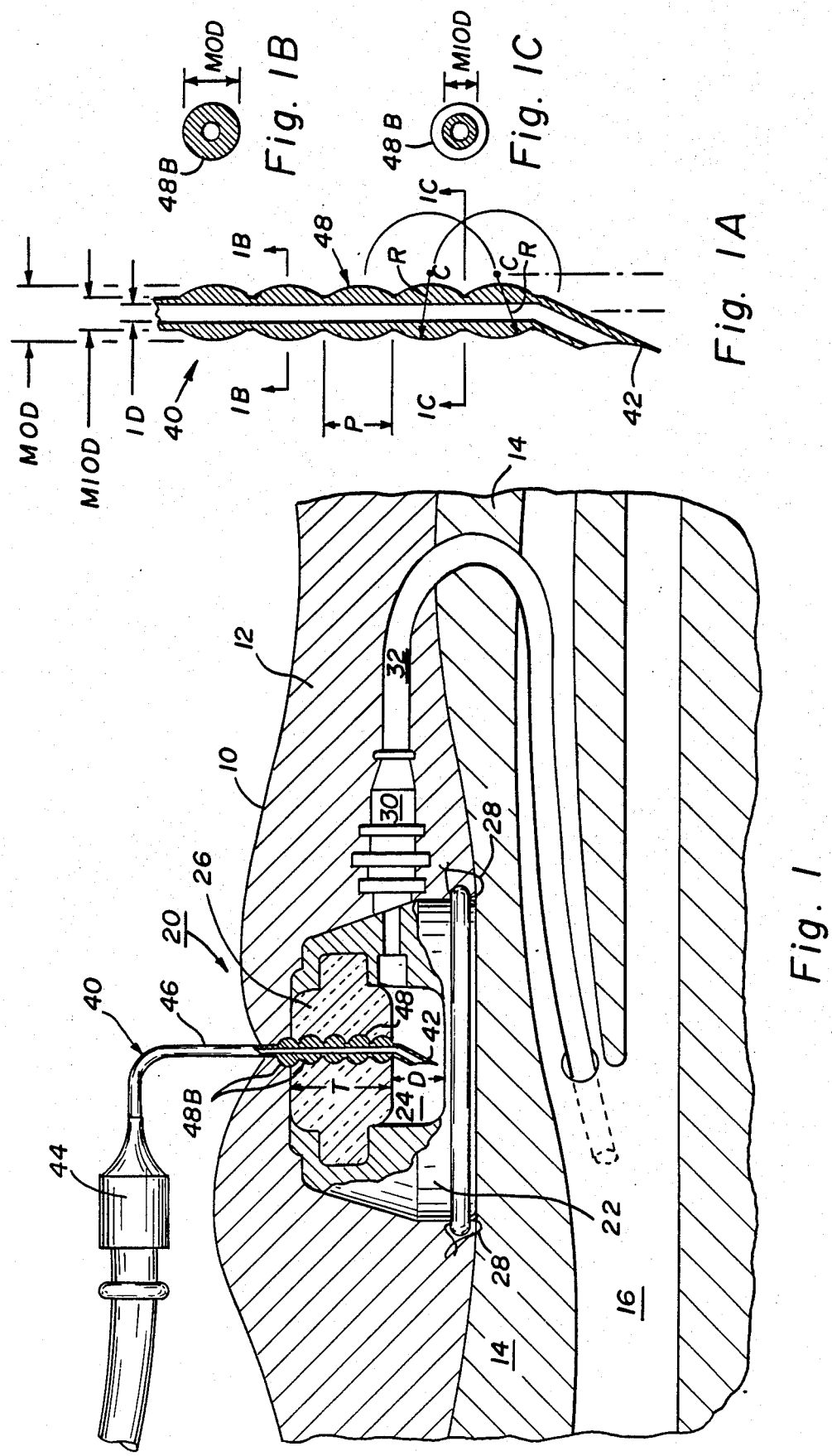
FIG. 1 is a perspective view, partly in section, of a subcutaneous venous device and needle system constructed in accordance with the principles of the present invention.

Referring to FIG. 1, there is depicted, in section, the interior of a patient, with the skin surface at 10, subcutaneous zone 12, deep fascia tissue 14, and with veins 16 shown in perspective.

A subcutaneous venous access device and needle system constructed in accordance with the present invention is generally indicated by the number 20. This system includes a port or device housing 22 defining a chamber 24 and having a septum 26. The chamber 24 extends a depth "D" (e.g., 0.165) below the septum 26, which has a thickness "T" (e.g., 0.35). The housing 22 has means securing it to the deep fascia 14 by sutures 28 and provides an exit fluid path from the chamber 24 through a coupling 30 to a catheter 32. This catheter 32 is surgically implanted into the vein 16, as shown.

As thus far described, the port or device 22-32 is more or less conventional. Commercial port devices of this general type are available from Cormed, Inc., under the trademark Mediport II Vascular Access Port and discussed in the medical literature, e.g., "Cancer," Vol. 57, #6, Mar. 15, 1986, pp. 1124–1129. Other such port devices are those available under the trademark PORT-A-CATH, manufactured by Pharmacia, Inc., 800 Centennial Avenue, Piscataway, N.J. 08854 and under the trademark NORPORT-SP, available from Norfolk Medical, 7307 N. Ridgeway, Skokie, Ill. 60076. The particular port depicted in FIG. 1 is similar to the PORT-A-CATH brand port. As such ports are commercially available and well known, we will not detail them here except as convenient in describing the improved system of the present invention.

The inventive system 20 further includes an infusion needle 40 which in this embodiment is an "L" shaped needle, having a non-coring point 42, a conventional "luer" lock 44, and a generally tubular shaft 46. The lower section 48 of the needle 40, that is, the section of the properly-seated needle as shown in FIG. 1, approximately equal in length to "D" plus "T" (i.e., the point 42 through the septum 26 and preferably perhaps a slightly greater distance to accommodate angling insertions) has its outer surface formed into a series of bulges or ridges 48B which present a positive upward slope to at least one part of the needle outer surface in or below the septum 26. This configuration of the outer surface of the section 48 has the advantageous result of greater resistance to accidental needle removal. The needle remains, however, easily and repeatedly removable and reinsertable, since the bulges present a smooth surface with sharp changes of direction occurring only at the innermost transitions (MIODs) along the length of the needle.

As shown best in FIGS. 1A and 1B, the bulged shaft section is generally symmetrical and circular in cross-section. One specifically preferred construction has an inside diameter of about 0.033 inch, a (one-tenth) maximum outside diameter (MOD) of about one-tenth of an inch, a vertical radius of curvature R (FIG. 1A) of five thirty-seconds of an inch, (measured from a center C offset from the shaft's center line by a distance equal to MOD) a minimum outside diameter (MIOD) of one-twentieth of an inch (the normal thickness of the remainder of the shaft) and a distance between minimum diameters P of five thirty-seconds of an inch.

Figure 2:
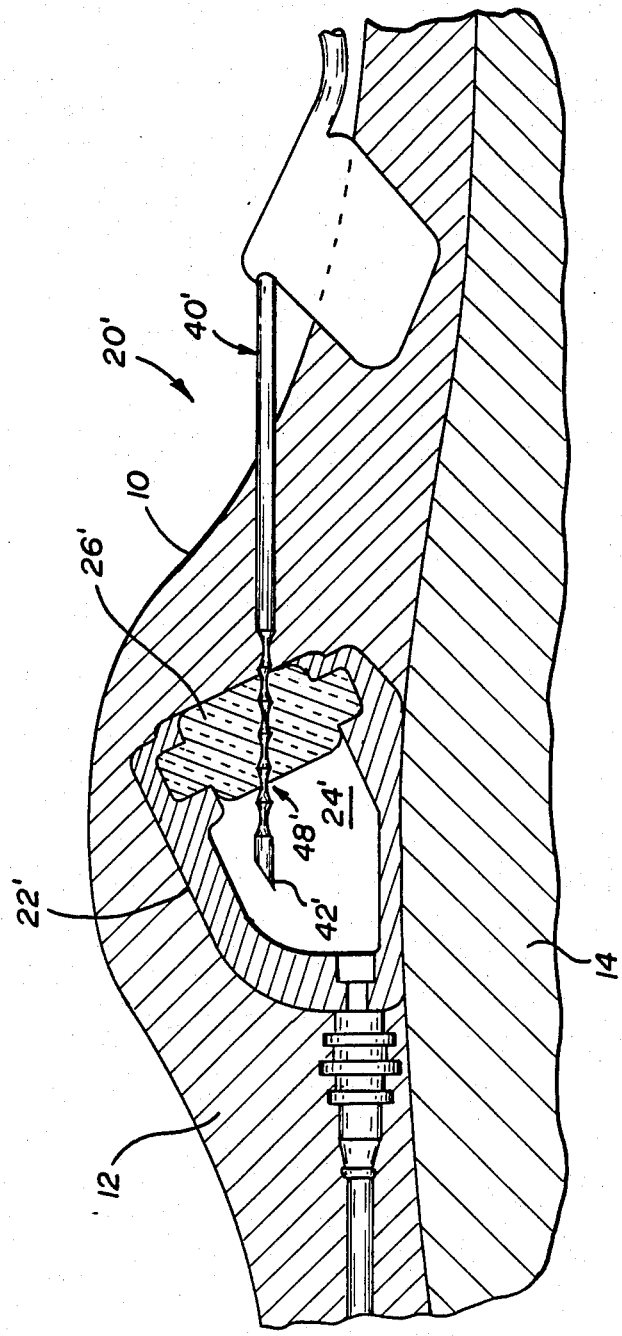
FIG. 2 is a perspective view, partly in section, of another type of subcutaneous venous device and needle system, also constructed in accordance with the principles of the present invention and constituting a second embodiment of the invention.

Referring to FIG. 2, there is depicted a second embodiment of the invention. In this case, the port housing 22 is constructed more or less as that of the aforementioned NORPORT-SP brand unit; that is, with a septum 26' facing at an angle to the base 22', whereby a noncoring straight butterfly needle 40' may be used. In accordance with the invention, the needle 40' has a modified outer surface over a section 48' of its shaft's length. In this case, the modified shape also presents reverse or backward sloping surfaces within and inside of the septum 26'. In this embodiment, these are formed by a series of indentations encircling the round shaft to form encircling valleys and ridges. One preferred example of this construction would have a maximum diameter of one-tenth of an inch, a minimum diameter of one-twentieth of an inch, a rate of curvature of five thirty-seconds of an inch, and a distance between ridges of five thirty-seconds of an inch.

Figures 3, 3A:
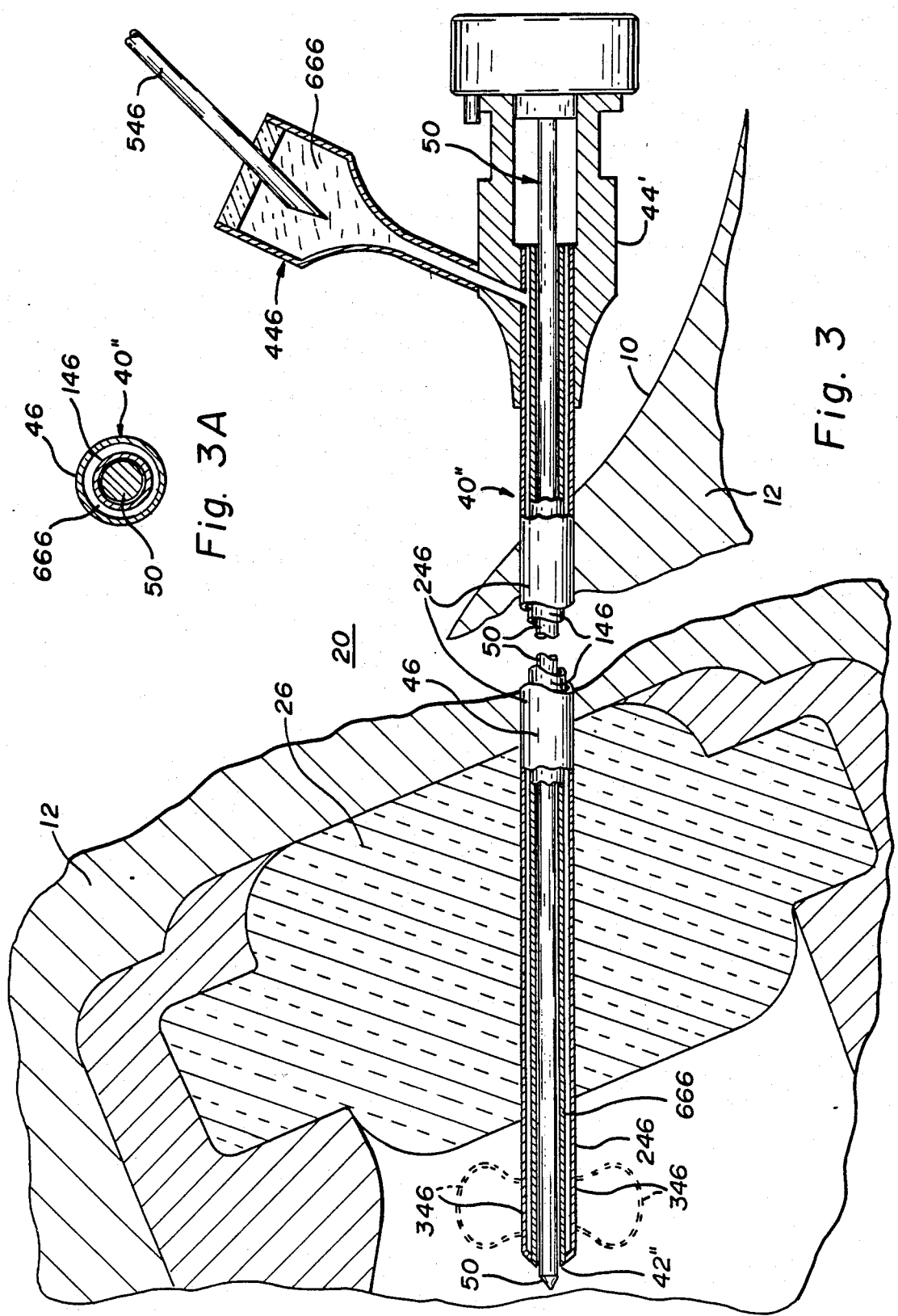
FIG. 3 is a perspective view, partly in section, and shown partly broken away, of a third embodiment of the present invention.
FIG. 3A is a sectional view of a part of the apparatus of FIG. 3 as seen from the line 3A—3A in FIG. 3.

Referring to FIG. 3, there is depicted another embodiment of the present invention. In this case, the needle apparatus 40" includes a stylet 50 which provides a noncoring point 42". The shaft 46" is double-walled with an inner wall 146 and a spaced-apart outer wall 246. This concentric wall construction is best seen in FIG. 3A. The two walls are preferably made of a rigid material such as plastic or thin metal and, as shown in FIG. 3, sealed together at the top and bottom of the shaft to provide a secondary fluid pressure pathway down the needle shaft to the area or section of the properly-set needle below the septum 26. A resiliently-elastic balloon segment 346 is provided in the outer wall 246. This may be formed by securing an elastic catheter-grade latex material across an annular opening in a metal-walled needle, or in the case of a plastic needle construction, by modifying the wall structure to render elastic the wall part 346. Means for manually increasing and decreasing pressure in the secondary path is provided by a secondary septum and housing apparatus 446 which commutes through the lock 44'. One convenient means for increasing or decreasing pressure in the secondary path is a standard syringe and needle 546 which may inject into the secondary septum. Such needles and syringes are usually readily available in hospitals and other places where infusion therapy is performed. The secondary pathway is preferably completely filled with a fluid, e.g., sterilized water, 666 so that the user may inflate and deflate the balloon 346 by injecting a predetermined quantity of additional water at the secondary septum 446. Since the rest of the closed container formed by the apparatus 446 and walls 146, 246 are made of relatively inelastic material, an injection of, say, 0.1 cc of water into the container will result in a ballooning of the balloon section 346 by a volume of approximately 0.1 cc. Removal of the needle 546 without removing any additional fluid will mean that the ballooned wall 346 will remain expanded to about 0.1 cc volume. Likewise, later insertion of the needle 546 and removal of 0.1 cc will reverse the process and allow the needle 40" to be easily removed.

Thus, precise remote control of the balloon 346 is readily provided to releasably lock the needle in place below the septum.

Referring now to FIGS. 4A and 4B, a further embodiment of the present invention is there depicted. In this embodiment, a stylet 50 is also employed; however, only a single-wall needle shaft 446 is employed. However, this shaft is constructed of material, at least at its point area 42A, which is resiliently deformable, e.g., a resilient plastic, and has a "natural" or unstressed shape, as shown in FIG. 4B. However, when the stylet 50 is inserted and locked against the luer lock 44, a conical point 50P of the stylet 50 engages and pushes lengthwise a decreased diameter front portion 42S at the point 42". This lengthens the needle's shaft and resiliently draws inward the portion 42A of the point, to present a smooth smaller diameter shaft, as shown in FIG. 4A, which allows for ease of penetration and withdrawal of the assembly 40". It should be noted that the section 42A would also be collapsed by the act of pulling it through the septum and the needle can be removed by exerting sufficient force in an emergency. However, use of the stylet to collapse the section 42A prior to removal of the needle is preferred.

The needle apparatus of the above-described embodiments would preferably have an overall length of approximately ¾"-1", a normal shaft outer diameter of about 18 gage (0.05") to 23 gage (0.025") with the "balloon" expanding to a diameter of approximately three times the normal shaft outer diameter.

While four particular embodiments of the invention have been shown and described, it will be obvious to those skilled in the art that changes and modifications may be made without departing from the invention and, therefore, the aim in the appended claims is to cover all such changes and modifications as fall within the true spirit and scope of the invention.

I claim:

1. In a subcutaneous venous access system of
   a port device defining a chamber with a septum for allowing a needle input into the chamber and a catheter output from the chamber:
   a needle assembly having a shaft section and a point, means for allowing the non-coring entry of the needle point through skin and the septum and which, when seated in the chamber, has a shaft segment which extends through the septum and into the chamber; and
   means for providing a changed outside diameter portion of the outside surface of the shaft in said segment;
   whereby said needle assembly may be seated into the chamber of the port device and said changed diameter section serve to prevent or reduce the possibility of said needle being unintentionally removed from the chamber and septum during use.

2. The system of claim 1, wherein said changed diameter is achieved by an increasing diameter wall portion in said shaft segment of said needle.

3. The system of claim 2, wherein said increased-diameter wall portion is achieved with a smooth, streamlined outer surface transition above and below said portion and the outside diameter of the shafts varies from a minimum to a maximum which, is at least maximum approximately twice the minimum diameter.

4. The system of claim 2, wherein said increased diameter section is created by a ballooning outward of the outer wall portion.

5. The system of claim 4, wherein said ballooning is selectably achieved by providing an elastic outer wall segment of said shaft at said portion, means defining a secondary fluid path through the needle shaft between said portion and a location remote from the needle point, and means for providing a second fluid pressure input into said secondary path at said remote location.

6. The system of claim 5, wherein said secondary pressure input includes a second septum, and the pressure may be increased or decreased to balloon out or retract said elastic wall segment by injecting a fluid through a removable needle into said second septum.

7. The system of claim 2, wherein said increased diameter section is reversably formed by spring action.

8. The system of claim 7, wherein said needle apparatus includes a central stylet which is sized and shaped to pass through the needle shaft and which when fully inserted causes the increased diameter section to reduce its diameter and when removed permits it to spring outward to increase its diameter.

9. The system of claim 1, wherein a plurality of successive changed diameter outer surface portions are formed along the length of the shaft in said section, to form a row of ridges which are gripped by said septum when the needle is properly seated in said port.

10. The system of claim 9 wherein the diameter of the ridges is at least approximately twice the minimum diameter between the ridges.

11. A needle apparatus for use with a subcutaneous venous access device of a type having a needle entry septum of a predetermined thickness and a chamber thereunder of a set depth under the septum, comprising:
   a needle shaft defining a fluid passageway to a needle point, said shaft having a section from the point rearward of a length equal to this set depth and the predetermined thickness, said shaft having an approximately constant diameter over the majority of its length;
   a non-coring needle point formed at the end of said shaft; and
   means for providing a different outside surface configuration of said shaft at said section for aiding in releasably securing the needle apparatus in said device when said needle point is driven into and through said septum and into said chamber for a distance.

12. The needle apparatus of claim 11, wherein said means for providing a different outside configuration provides a series of successive ridges along at least a portion of the length of said section.

13. The needle apparatus of claim 11, wherein said means for providing a change in the outside configuration provides an expanded bulge therein near the point, which bulge is located under the septum when the needle has passed through it and entered the chamber.

14. The needle apparatus of claim 13, wherein said means includes means for selectively forming and retracting said bulge.

15. The needle apparatus of claim 14, wherein said selectable forming and retracting means is a stylet which is sized to be inserted into said shaft and when so inserted also provides the non-coring feature of the point.

16. The needle apparatus of claim 15, wherein said stylet has a conical point and said needle point has a decreased diameter which mates with said conical point, whereby the stylet when pressed downward to the point presses against the needle point and axially stresses the needle shaft, and the section includes a flexible wall section which forms said bulge when not axially stressed, but which when axially stressed tends to retract, whereby placing and pressing the stylet into the shaft substantially retracts the bulge for insertion and retraction, but removal of the stylet allows the bulge to form.

* * * * *